United States Patent [19]

Buzzetti et al.

[11] Patent Number: 5,130,472
[45] Date of Patent: Jul. 14, 1992

[54] TOTAL SYNTHESIS OF ERBSTATIN ANALOGS

[75] Inventors: Franco Buzzetti, Monza; Angelo Crugnola, Varese; Paolo Lombardi, Cesate, all of Italy

[73] Assignee: Farmitalia Carlo Erba S.r.l., Milan, Italy

[21] Appl. No.: 608,505

[22] Filed: Nov. 2, 1990

[30] Foreign Application Priority Data

Jan. 16, 1990 [GB] United Kingdom ............... 9000939

[51] Int. Cl.$^5$ ............... C07C 233/18; C07C 69/017; C07C 233/23
[52] U.S. Cl. ............... 560/252; 564/219; 562/445; 560/40
[58] Field of Search ............... 564/219; 560/252; 514/630, 546

[56] References Cited

U.S. PATENT DOCUMENTS 3,056,790 10/1962 Cannon ............... 260/287

FOREIGN PATENT DOCUMENTS

89/04659 6/1989 Int'l Pat. Institute.

OTHER PUBLICATIONS

Mulzer et al., Angew. Chem. Int. Ed. 16, pp. 255-256 (1977).
Mulzer et al., "The Decarboxylative Dehydration of 3-Hydroxylcarboxylic Acids with Dimethylformamide-dimethylacetal-Evidence for a Zwitterionic Intermediate", Tetrahedron Letters No. 21, pp. 1909-1912, 1979, Great Britain.
Shaw et al., "Stereochemistry of the β-Phenylserines: Improved Preparation of Allophenylserine", J. Am. Chem. Soc. 75, pp. 3421-3424, 1953, Ames, Iowa.
McOmie et al., "Demethylation of Aryl Methyl Ethers by Boron Tribromide", Tetrahedron, vol. 74, pp. 7789-7797, Sep. 1967, Great Britain.

*Primary Examiner*—Jose G. Dees
*Assistant Examiner*—B. Frazier
*Attorney, Agent, or Firm*—Nikaido, Marmelstein, Murray & Oram

[57] ABSTRACT

The present invention relates to a new process for the preparation of Erbstatin and Erbstatin analogs, which can be represented by the following formula (I)

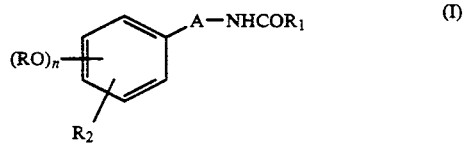

wherein
R is hydrogen, a lower alkyl or a lower alkanoyl group;
n is an integer of 1 to 3;
A is —CH=CH— or —CH$_2$—CH$_2$—;
R$_1$ is hydrogen or a lower alkyl group, and
R$_2$ is a hydrogen or halogen atom.

9 Claims, No Drawings

TOTAL SYNTHESIS OF ERBSTATIN ANALOGS

BACKGROUND OF THE INVENTION

The present invention relates to a new process for the preparation of Erbstatin and Erbstatin analogs, which can be represented by the following formula (I)

with the treatment of 2,5-dimethoxybenzaldehyde with nitromethane to give a nitrostyrene, which after conjugate addition of thiophenol gives a thioether. Hydride reduction and N-formylation provides a saturated formamide, which is converted to an enamide by an oxidation and elimination process. Final ether cleavage gives Erbstatin.

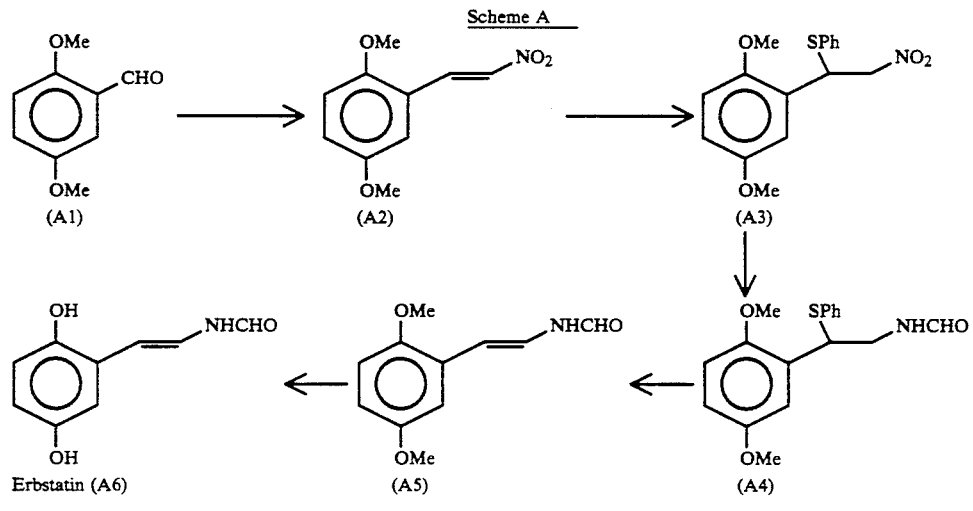

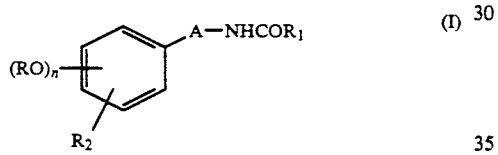

wherein
R is hydrogen, a lower alkyl or a lower alkanoyl group;
n is an integer of 1 to 3;
A is —CH=CH— or —CH$_2$—CH$_2$—;
R$_1$ is hydrogen or a lower alkyl group, and
R$_2$ is a hydrogen or halogen atom.

In the present invention the lower alkyl group and the lower alkanoyl group means that the alkyl group part is a branched or straight alkyl group having 1 to 5 carbon atoms.

When n is 2 or 3, each single —OR group may be the same or different.

The halogen atom includes any one of fluorine, chlorine, bromine and iodine atoms.

The scope of the invention includes also all the possible isomers (e.g. Z and E isomers) of the compounds of formula (I) and the mixtures thereof.

Erbstatin is an antibiotic, produced by a strain of Streptomycetes [EP-A-213320], which inhibits tyrosine-specific protein kinase, e.g. it inhibits the phosphorylation of the epidermal growth factor receptor [J. Antibiot. 1986, 39, 170]. The Erbstatin analogs, falling within the scope of formula (I) above, are disclosed by EP-A-238868 and are described as having similar biological properties.

The introduction of an acylaminovinyl group in a phenol compound is a well known process in the art. This type of substitution has been previously achieved by many step procedures. The method described by W. K. Anderson et al. in J. Org. Chem. 52, 2945 (1987), for instance, begins as is shown in scheme A herebelow According to the process described in EP-A-238868, the acylaminovinylation procedure is alternatively carried out as shown in following scheme B.

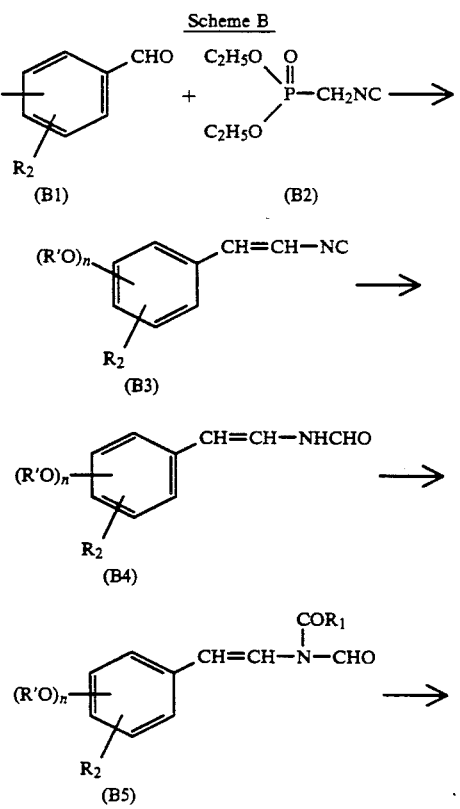

-continued
Scheme B

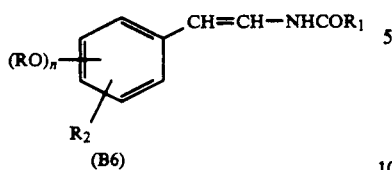

Scheme C

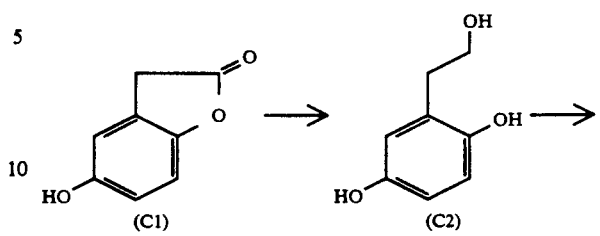

wherein

R' is lower alkyl or lower alkanoyl and $R_1$, $R_2$ and n are as defined above.

The benzaldehyde of formula (B1) is subjected to a Wittig reaction with diethyl isocyanomethylphosphite of formula (B2) to give the isocyanovinyl-phenol compound of formula (B3), which is hydrolyzed to obtain the formylaminovinylphenol compound of formula (B4). In order to obtain acylaminovinyl-phenol compounds of general formula (B6) other two steps are necessary, that is, an acylation and a deformylation reaction. So as to obtain the acylaminoethylene analogs (B'7). The compounds of formula (B4) are hydrogenated in the presence of a catalyst to give the corresponding compounds (B'4)

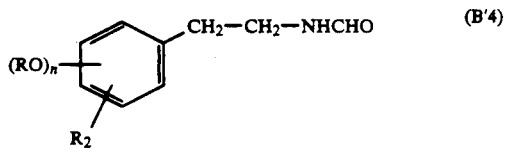

which are further subjected to acylation and deformylation reaction affording compounds of formula (B'7)

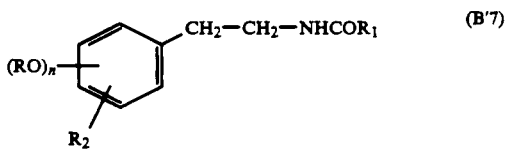

Although the synthesis method described in EP-A-238868 has the advantage of being short, from the industrial point of view it has the following drawbacks: (a) use of commercially non available reagents, e.g. diethyl isocyanomethylphosphite of formula (B2); (b) use of expensive and highly sensitive bases, e.g. sodium bis(trimethylsilyl)amide is used in the Wittig reaction; and (c) application of a laboratory scale chromatographic procedure, i.e. preparative T.L.C.

A further method for the preparation of Erbstatin has been described by D. G. Hangauer in Tetrahedron Letters 27, 5799 (1986).

Noteworthy is that in this case a phenylactic acid derivative is used as starting material, instead of a benzaldehyde derivative.

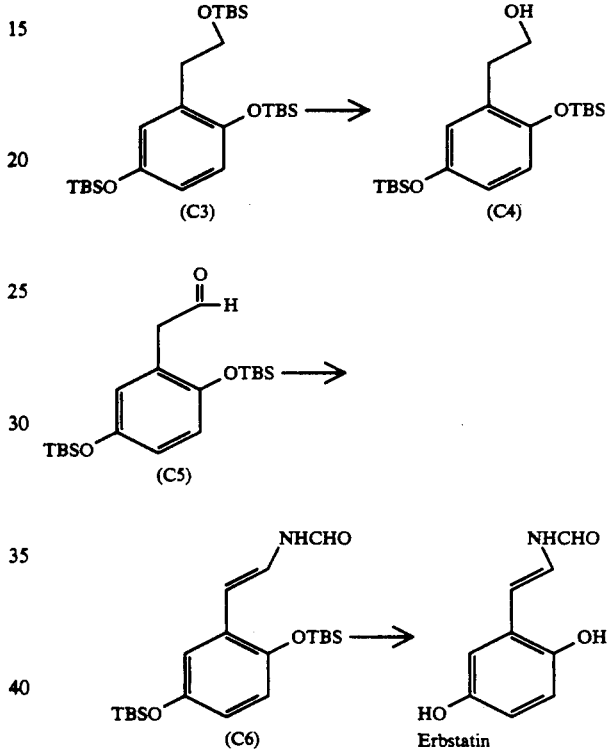

wherein TBS means t-butyldimethylsilyl.

The commercially available lactone (C1) is reduced with DIBAH to the triol (C2), which is protected by transformation into the trisilylether (C3).

Selective cleavage with HF and partial oxidation with pyridinium chlorochromate provides the aldehyde (C5). Condensation with DMF gives compound (C6), which is deprotected with $Bu_4NF$ to give Erbstatin. Although this method possesses a good overall yield (38%), from the industrial point of view many objections can be raised, for example: application of several chromatographic purifications, use of highly corrosive HF, and use of special chromatographic techniques.

Another 6-step stereoselective synthesis of Erbstatin, starting from the commercially available 2,5-dihydroxycinnamic acid, has been described by R. L. Dow and M. J. Flynn (Pfizer Inc.) in Tetrahedron Letters 28, 2217 (1987), as shown in the following scheme D.

Scheme D

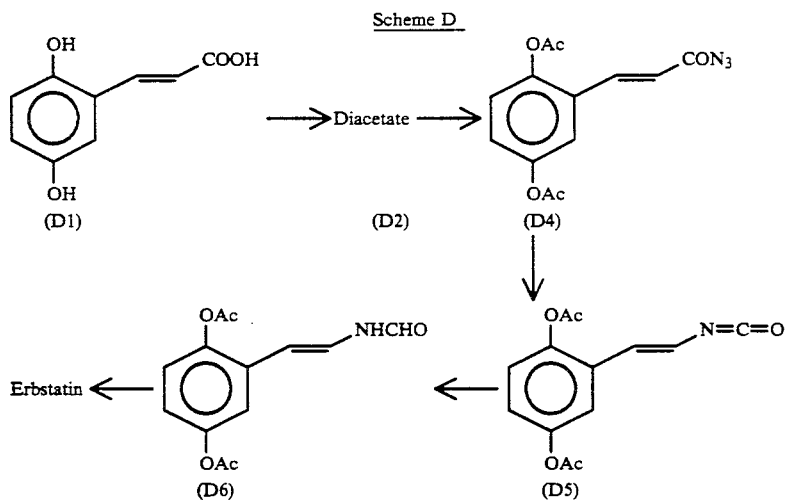

Accordingly, 2,5-dihydroxycinnamic acid is acetylated and then transformed in acyl azide (D4) via its acyl chloride. Thermal rearrangement generates the isocyanate (D5), which is reduced selectively to the formamide (D6). Final deprotection provides Erbstatin. Although the overall yields are good (36%) this synthetic method has the disadvantage of using sodium azide, which under certain conditions is highly explosive.

In conclusion none of the four above described synthesis methods meets all the criteria requested for an industrial process, especially from the point of view of safety, large-scale production, availability of intermediates and reagents at commercial quantities and prices, and of industrially acceptable purification methods. Therefore there is the need to develop a new synthetic method that overcomes these limitations and fulfills the criteria of a real industrial process.

SUMMARY OF THE INVENTION

The present invention provides a solution of such industrial problem. Accordingly, the present invention provides a new process for the preparation of a compound of formula (I) as herein defined, said process comprising the dehydrative decarboxylation of an α-acylamino-β-hydroxy acid of formula (II):

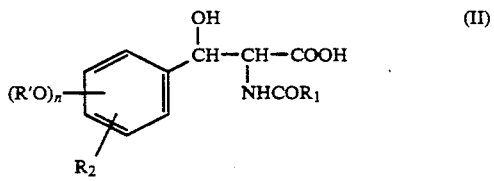

wherein

R' is lower alkyl and $R_1$, $R_2$ and n are as defined above, followed, if required, by conversion of the or each group group R'O into a hydroxy group so as to obtain a compound of formula (I), wherein A is a —CH═CH— chain and $R_1$, $R_2$ and n are as defined above and R is hydrogen or a lower alkyl group;

and, if desired, reducing a compound of formula (I) wherein A is a —CH═CH— chain so as to obtain a corresponding compound of formula (I) wherein A is a —CH$_2$—CH$_2$— chain; and/or, if desired acylating a compound of formula (I) wherein R is hydrogen and n, A, $R_1$ and $R_2$ are as defined above so as to obtain a compound of formula (I) wherein R is lower alkanoyl and n, A, $R_1$ and $R_2$ are as defined above; and/or, if desired, separating a mixture of isomers of compounds of formula (I) into the single isomers.

The present process is particularly suitable for the preparation of compounds of formula (I) in which R is hydrogen or $C_1$-$C_4$ alkyl, $R_1$ is hydrogen or $C_1$-$C_4$ alkyl and $R_2$ is hydrogen. In preferred such compounds R, $R_1$ and $R_2$ are all hydrogen atoms. The process of the present invention can therefore be applied to the production of Erbstatin and Erbstatin derivatives, i.e. compounds of formula (I) in which n is 2, $R_2$ is hydrogen and the two R'O groups are located at the 2- and 5-positions of the benzene ring.

The dehydrative decarboxylation of an α-acylamino-β-hydroxy acid of formula (II) is a new process. Indeed as far as we know, never before has an α-acylamino-β-hydroxy acid been subjected to a dehydrative decarboxylation in order to obtain an enamide. Up to now only β-hydroxy acids have been subjected to dehydrative decarboxylation with the aim to provide the respective olefin derivatives, as described for example by Shoji Hara et al. in Tetrahedron Letters 19, 1545 (1975) and by Johann Mulzer et al. in Angew. Chem. Int. Ed. 16, 255 (1977).

The dehydrative decarboxylation of an α-acylamino-β-hydroxy acid of formula (II) can be performed by reaction with a dimethylformamide (DMF) acetal in a suitable inert solvent, e.g. chloroform, dichloromethane or 1,2-dichloro ethane.

Preferably the reaction is carried out with an excess of N,N-dimethylformamide dimethyl acetal (about 6 mol equivalents) in dry chloroform solution. The reaction temperature may range from about 0° C. to about 100° C., however the reflux temperature is the preferred one. The enamide of formula (I) thus obtained may be isolated by evaporation and filtration through a silica gel column. Alternatively the dehydrative decarboxylation of a compound of formula (II) can be performed by redox condensation with triphenylphosphine and diethyl azodicarboxylate. The reaction can be performed in an ethereal organic solvent, e.g. in di(lower) alkyl ether, in particular diethyl ether, or in a cyclic aliphatic ether, preferably in tetrahydrofuran; at a temperature ranging from about −10° C. to about 40° C. The reaction time takes from about 10 minutes to about 2 hours.

After the evaporation of the solvent the raw product may be separated from the triphenylphosphine oxide and the hydrazoester formed by selective extraction with pentane/ether. Alternatively the product may be purified by filtration through a short silica gel column. An R'O-group in a compound of formula (II) can also be considered as a protected hydroxy group, in the form of an etherified hydroxy group. Thus, the removal of the hydroxy protecting group(s) in a compound of formula (I), i.e. the deprotection of a hydroxyl group in which such group is in etherified form, can be achieved by methods well known in organic chemistry. For example in the case of a phenolic methyl ether the cleavage can be carried out for example with boron tribromide as described by J. F. W. McOmie in Tetrahedron 24, 2289 (1968). It is advisable to use one mole of boron tribromide per ether group together with an extra mole of reagent for each group containing a potentially basic N or O. The reaction may be performed in an inert organic solvent such as methylenechloride, pentane or benzene, under a nitrogen atmosphere at temperatures ranging from about $-78°$ C. to about room temperature. The reaction mixture is quenched by water addition and the product extracted with an organic solvent. The product is further purified by crystallization or by filtration through a short silica gel column.

Reduction of a compound of formula (I), wherein A is a $-CH=CH-$ chain so as to obtain a corresponding compound of formula (I) wherein A is a $-CH_2-CH_2-$ chain can be performed e.g. by hydrogenation in the presence of a catalyst.

The hydrogenation can be carried out by a per se known reaction which is generally used for the hydrogenation of an ethylene chain. For instance by reaction with hydrogen in the presence of a catalyst such as platinum oxide or Pd/C and by using as solvent for example a lower alkanol, in particular methanol, ethanol or isopropanol, or water.

Compounds of formula (I) wherein R is a lower alkanoyl group and $R_1$, $R_2$, A and n are as defined above, can be obtained from the corresponding compounds of formula (I) in which R is hydrogen by reaction with a reactive derivative of a suitable aliphatic carboxylic acid, such as an anhydride or halide as described below.

The optional separation of a mixture of isomers of compounds of formula (I) can be carried out by known methods.

A compound of formula (II) can be obtained by acylating an amino compound of formula (III)

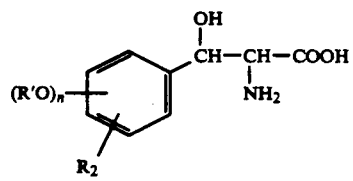

wherein

R', $R_2$ and n are as defined above, with a suitable acylating agent, according to known methods. For example a compound of formula (II) in which $R_1$ is hydrogen can be obtained by reaction with excess of acetic formic anhydride; at temperatures ranging from about $-15°$ C. to about $25°$ C.

A compound of formula (II) in which $R_1$ is lower alkyl can be obtained for instance by reaction with a reactive derivative of a suitable aliphatic carboxylic acid; such as an anhydride or halide; in the presence of a basic agent at temperatures ranging from about $0°$ C. to about $50°$ C. Preferably the acylation is carried out by reaction with the respective anhydride in the presence of an organic base, such as pyridine.

A compound of formula (III) can be obtained by reacting a compound of formula (IV)

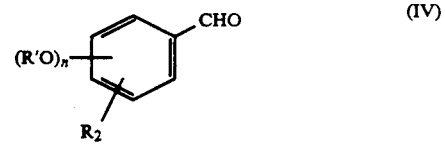

wherein

R', $R_2$ and n are as defined above, with glycine. This condensation may be carried out e.g. according to K. N. F. Shaw et al. (J. Am. Chem. Soc. 75, 3421. 1953).

The ratio of the reagents is not critical, but in general 2 mol equivalents of the aldehyde component are employed. The condensation may be performed in water or in an aqueous solvent such as aqueous ethanol in the presence of a basic catalyst. Preferably the condensation is carried out in water in the presence of 1.5 mol equivalents sodium hydroxide. The reaction temperatures may vary from about $0°$ C. to about $50°$ C., with a temperature range from $15°$ C. to $25°$ C. being the preferred. During the condensation a mixture of threo- and erythrodiastereomers is formed, which ratio increases with time. In order to obtain only the threo form, long reaction times ranging from 20 to 24 h are to be chosen. After the condensation reaction the N-benzal intermediate formed is hydrolyzed without isolation by treatment with hydrochloric acid at temperatures ranging from about $10°$ to about $25°$ C.

The compounds of general formula (IV) may be obtained according to known methods from compounds of general formula (V)

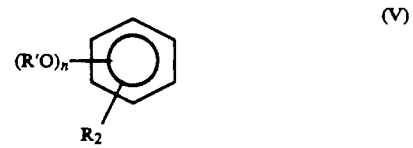

wherein

R', $R_2$ and n are as defined above. For example the phenolic compound of formula (V) may be treated with chloroform and alkali hydroxides in aqueous or hydroalcoholic solution according to the well known method of Reimer-Tiemann.

The compounds of formula (V) are known or may be obtained by known methods from known compounds. For example, one of the compounds of formula (V) in which R'=$R_2$=H and n=2, is the well known hydroquinone. Considering that: (a) the starting compounds of formula (V) are either commercially available products or easily obtainable from such products; (b) the reagents and auxiliaries employed are safe and inexpensive; (c) the reaction and work-up conditions are industrially feasible; (d) no column chromatography or other special purification techniques are required; we can state that the process according to the present invention is efficient, safe, economical and amenable to large scale production. Moreover in the preparation for example of Erbstatin, i.e. a compound of formula (I) in which A is —CH=CH—, n is 2 and R, $R_1$ and $R_2$ are hydrogen, the versatile and stereoselective 4-step synthesis method according to the present invention works with 42% overall yield starting from the commercially available 2,5-dimethoxybenzaldehyde. Furthermore if one compares the present method with the method of W. K. Anderson et al. (Scheme A), although both make use of the same starting material and work with the same yield, the new method has the advantage of using only 4 steps, instead of 7 steps, without using such dangerous reagents, like nitromethane.

The compounds of formula (I) prepared by the process of the present invention may be formulated as a pharmaceutical composition. The composition also comprises a pharmaceutically acceptable carrier or diluent.

The following Examples illustrate but do not limit the invention.

EXAMPLE 1 threo-3-(2,5-dimethoxyphenyl) serine (III, R'=$CH_3$, $R_2$=H, n=2)

To a solution of glycine (7.51 g, 0.1 mol) and 2,5-dimethoxybenzaldehyde (33.24 g, 0.2 mol in 50% ethanol (80 ml)) is added sodium hydroxide (14 g, 0.35 mol) dissolved in 40 ml of water. The reaction mixture is stirred for 24 h, then acidified with 5M HCl (90 ml, 0.45 mol) to about pH 2. The reaction mixture is extracted with $CHCl_3$. The organic phase contains about 7.51 g 2,5-dimethoxybenzaldehyde (100% recovery) which can be recycled without further purification.

The aqueous phase is brought to the isoelectric point, that is to pH 5.5–6. The resulting precipitate is filtered after cooling, washed with water and dried under vacuum. Thus 16.89 g (70% yield) of almost pure title compound is obtained with m.p. 176°–8° C. (dec.).

From the mother liquor upon concentration other title compound can be obtained. The 2nd mother liquor contains about 5–10% raw erythro isomer.

The proceeding of the reaction and the threo/erythro isomer ratio is monitored by cellulose TLC using n-butanol/acetone/30% ammonia/water 8:1:1:7 for development.

$C_{11}H_{15}$—$NO_5$ requires: C; 54.76, H; 6.27, N; 5.81. Found: C; 54.55, H; 6.13, N; 5.55.

NMR δ (DMSO-$d_6$): 3.35 (d, J=3.2 Hz, 1H, CH—$NH_2$), 3.70 (s, 3H, $OCH_3$), 3.75 (S, 3H, $OCH_3$), 5.45 (d, J=3.2 Hz,1H,CH—OH 6.60–7.10 (m, 3H, arom), According to the above described procedure the following compounds can be obtained:
threo-3-(2-methoxyphenyl) serine;
threo-3-(3-methoxyphenyl) serine;
threo-3-(4-methoxyphenyl) serine;
threo-3-(2,3-dimethoxyphenyl) serine;
threo-3-(2,4-dimethoxyphenyl) serine;
threo-3-(2,6-dimethoxyphenyl) serine;
threo-3-(3,4-dimethoxyphenyl) serine;
threo-3-(3,5-dimethoxyphenyl) serine, and
threo-3-(2-methoxy-5-bromophenyl) serine.

EXAMPLE 2 threo-3-(2,5-dimethoxyphenyl)-N-formylserine (II, R'=$CH_3$, $R_1$=$R_2$=H, n=2)

To a solution of threo-3-(2,5-dimethoxyphenyl) serine (24,13 g, 0.1 mol) in 99% formic acid (20 ml) is added acetic anhydride (5 ml) and the resulting solution stirred for 2 h at room temperature. Then water is added and the mixture evaporated under vacuum. The residue is crystallized from water thus giving 22.89 g (85%) of almost pure title compound with m.p. 150°–1° C. (dec.).

$C_{12}H_{15}NO_6$ requires: C: 53.53, H: 5.62, N: 5.20. Found: C: 53.15, H: 5.51, N: 5.01, NMR δ (DMSO-$d_6$): 3.65 (s, 3H, $OCH_3$), 3.75 (s, 3H, $OCH_3$) 4.65 (dd, J=7.5 Hz, J=2 Hz, 1H, CHN), 5.45 (d, J=2 Hz, 1H, CH—O—), 6.6–7.1 (m, 3H, arom), 7.8–8.7 (m, 2H, NH, CHO), MS m/z: 269

Using the same procedure the following compounds can be obtained:
threo-3-(2-methoxyphenyl)-N-formylserine;
threo-3-(3-methoxyphenyl)-N-formylserine;
threo-3-(4-methoxyphenyl)-N-formylserine;
threo-3-(2,3-dimethoxyphenyl)-N-formylserine;
threo-3-(2,4-dimethoxyphenyl)-N-formylserine;
threo-3-(2,6-dimethoxyphenyl)-N-formylserine;
threo-3-(3,4-dimethoxyphenyl)-N-formylserine;
threo-3-(3,5-dimethoxyphenyl)-N-formylserine; and
threo-3-(2-methoxy-5-bromophenyl)-N-formylserine.

EXAMPLE 3

(E)-N-[2-(2,5-dimethoxyphenyl)ethenyl] formamide (I, R=$CH_3$, $R_1$=$R_2$=H, A=—CH=CH—, n=2)

A solution of threo-3-(2,5-dimethoxyphenyl)-N-formylserine (26.93 g, 0.1 mol) and N,N-dimethylformamide dimethyl acetal (71 g, 0.6 mol) in dry chloroform (500 ml) is heated at reflux temperature for 2 h. The reaction mixture is evaporated under vacuum, the residue dissolved in chloroform and filtered through a short silica gel column. The eluate is evaporated under vacuum giving almost pure title compound in 85% yield (17.61 g) with m.p. 84°–5° C. (dec.).

$C_{11}H_{13}NO_3$ requires: C; 63.75, H; 6.32, N; 6.76, Found: C; 63.65, H; 6.21, N; 6.65, NMR δ ($CHCl_3$): 3.70 (s, 3H, $OCH_3$), 3.75 (s, 3H, $OCH_3$) 6.50 (d, J=15 Hz, 1H, H-7), 6.75 (m, 2H, H-5, H-6), 6.95 (d, J=3 Hz, 1H, H-3), 7.60 (dd, J=12 Hz, J=15 Hz, 1H, H-8), 8.15 (s, 1H, CHO), 9.20 (br, 1H, NH).

By proceeding analogously the following compounds can be prepared:
(E)-N-[2-(2-methoxyphenyl)ethenyl]formamide;
(E)-N-[2-(3-methoxyphenyl)ethenyl]formamide;
(E)-N-[2-(4-methoxyphenyl)ethenyl]formamide;
(E)-N-[2-(2,3-dimethoxyphenyl)ethenyl]formamide;
(E)-N-[2-(2,4-dimethoxyphenyl)ethenyl]formamide;
(E)-N-[2-(2,6-dimethoxyphenyl)ethenyl]formamide;
(E)-N-[2-(3,4-dimethoxyphenyl)ethenyl]formamide;
(E)-N-[2-(3,5-dimethoxyphenyl)ethenyl]formamide, and
(E)-N-[2-(2-methoxy-5-bromophenyl)ethenyl]formamide.

EXAMPLE 4

(E)-N-[2-(2,5-dimethoxyphenyl)ethenyl]formamide (I, R=$CH_3$, $R_1$=$R_2$=H, A=—CH=CH—, n=2)

Herebelow we describe an alternative method of dehydrative decarboxylation that utilizes the principle of the redox condensation.

To a stirred solution of threo-3-(2,5-dimethoxyphenyl)-N-formylserine (26.93 g, 0.1 mol) in anhydrous THF (100 ml) is added a solution of triphenylphosphine (26.23 g, 0.1 mol) in THF (60 ml) under a nitrogen atmosphere at 0°-5° C. The resulting mixture is treated dropwise with a solution of diethyl azodicarboxylate (17.42 g, 0.1 mol) in THF (60 ml) at 0°-5° C. during a period of 20 min. The progress of the reaction is indicated by the slight warming of the mixture and the decoloration. The mixture is stirred for an additional 30 min. at 0°-5° C. and 30 min. at room temperature. After stripping off the solvent under vacuum the residue is dissolved in chloroform and the solution filtered through a short silica gel column. The filtrate is evaporated under vacuum to dryness providing almost pure title compound in 70% yield with m.p. 84°-5° C. Using the same procedure the following compounds can be prepared:

(E)-N-[2-(2-methoxyphenyl)ethenyl]formamide;
(E)-N-[2-(3-methoxyphenyl)ethenyl]formamide;
(E)-N-[2-(4-methoxyphenyl)ethenyl]formamide;
(E)-N-[2-(2,3-dimethoxyphenyl)ethenyl]formamide;
(E)-N-[2-(2,4-dimethoxyphenyl)ethenyl]formamide;
(E)-N-[2-(2,6-dimethoxyphenyl)ethenyl]formamide;
(E)-N-[2-(3,4-dimethoxyphenyl)ethenyl]formamide;
(E)-N-[2-(3,5-dimethoxyphenyl)ethenyl]formamide, and
(E)-N-[2-(2-methoxy-5-bromophenyl)ethenyl]formamide.

EXAMPLE 5

(E)-N-[2-(2,5-dihydroxyphenyl)ethenyl]formamide (Erbstatin) (I, R=R$_1$=R$_2$=H, A=—CH=CH—, n=2)

To a stirred solution of (E)-N-[2-(2,5-dimethoxyphenyl) ethenyl] formamide (2.071 g, 10 mmol) in anhydrous dichloromethane (100 ml) is added, at −78° C. under nitrogen over a period of 10 min, a 1.0M solution of boron tribromide in dichloromethane (30 ml, 30 mmol). The resulting mixture is stirred for another 1 h at −78° and then allowed to warm to room temperature. After stirring for 1.5 h at 20°-25° C. the mixture is cooled to −10° C. and then quenched by the dropwise addition of water (100 ml) over a 10 min period. After addition of ethyl acetate (100 ml) the organic layer is separated, washed with water, dried with Na$_2$SO$_4$ and evaporated under vacuum to dryness. After venting with nitrogen the residue is dissolved in 80 ml of CHCl$_3$/MeOH 10% and the solution diluted with CHCl$_3$ (60 ml) to faint turbidity. The mixture is kept for 5 h at 0°-5° C., the precipitate filtered and dried at 20°-25° C. under vacuum. Thus 14.34 g (80% yield) of pure title compound is obtained with m.p. 149°-153° C.

C$_9$H$_9$NO$_3$ requires: C; 60.33, H; 5.06, N; 7.82,
Found: C; 60.25, H; 5.01, N; 7.75.

IR (KBr) 3600-3100, 1665, 1635, 1595, 1525, 1505, 1255, 1190, 945, 770 cm$^{-1}$.

NMR δ (acetone-d$_6$): 6.49 (d, J=15 Hz, H-7), 6.53 (dd, J=9 Hz, J=3 Hz, H-5), 6.68 (d, J=9 Hz, H-6), 6.83 (d, J=3 Hz, H-3), 7.62 (dd, J=15 Hz, J=11 Hz, 1H, H-8, 7.65-7.97 (S br, 2H, OH), 8.17 (S, 1H, CHO), 9.15-9.30 (S br, 1H, NH).

According to the above described procedure the following compounds can be prepared:
(E)-N-[2-(2-hydroxyphenyl)ethenyl]formamide, m.p. 119° C.;
  IR(KBr): 3350, 3200, 1660, 1645, 1530, 1455 cm$^{-1}$,
  NMR δ: 6.50 (d, 1H), 6.82 (dt, 1H), 6.89 (dd, 1H), 6.99 (dt, 1H), 7.32 (dd, 1H), 7.72 (dd, 1H), 8.01 (br, 1H), 8.21 (S, 1H), 8.60 (br, 1H).

(E)-N-[2-(2,3-dihydroxyphenyl)ethenyl]formamide
  IR cm$^{-1}$(KBr): 3350, 1670, 1655, 1485, 1390,
  NMR δ (acetone-d$_6$): 6.50 (d, 1H), 6.6-7.0 (m, 3H), 7.70 (dd, 1H), 8.20 (S, 1H), 8.50 (br, 1H), 9.25 (br, 1H).

(E)-N-[2-(3,4-dihydroxyphenyl)ethenyl]formamide
  m.p. 184°-6° C.
  IR cm$^{-1}$ (KBr): 3340, 3150, 1670, 1640, 1600, 1500,
  NMR δ (acetone-d$_6$): 6.20 (d, 1H), 6.7-6.9 (m, 3H), 7.35 (d, 1H), 8.19 (S, 1H), (E)-N-[2-(2-hydroxy-5-bromophenyl)ethenyl]formamide
  m.p. 147° C.,
  IR cm$^{-1}$ (KBr): 3370, 3200, 1685, 1675, 1640, 1515,
  NMR δ (acetone-d$_6$): 6.45 (d, 1H), 6.85 (d, 1H), 7.15 (dd, 1H), 7.50 (d, 1H), 7.90 (dd, 1H), 8.15 (S, 1H), 9.00 (S, 1H), 9.35 (br, 1H), (E)-N-[2-(3-hydroxyphenyl)ethenyl]formamide;
(E)-N-[2-(4-hydroxyphenyl)ethenyl]formamide;
(E)-N-[2-(2,4-dihydroxyphenyl)ethenyl]formamide;
(E)-N-[2-(2,6-dihydroxyphenyl)ethenyl]formamide, and
(E)-N-[2-(3,5-dihydroxyphenyl)ethenyl]formamide.

EXAMPLE 6

(2-formylaminoethyl)-2,5-dihydroxybenzene (I, R=R$_1$=R$_2$=H, A=—CH$_2$—CH$_2$—, n=2)

To a solution of (E)-N-[2-(2,5-dihydroxyphenyl)ethenyl] formamide (1.792 g, 10 mmol) in methanol (40 ml) palladium on activated carbon (0.18 g) is added. The resulting mixture is vigorously stirred in a hydrogen atmosphere for about 2 h at room temperature. Then the catalyst is filtered off, the reaction solution evaporated under reduced pressure and the residue crystalized from water. Thus 1.613 g (90% yield) of pure title compound are obtained.

C$_9$H$_{11}$NO$_3$ requires: C; 59.66, H; 6.12, N; 7.73, Found: C; 59.59, H; 6.05, N; 7.65, IR (KBr): 3340, 1640, 1510 cm$^{-1}$.

Following the above described procedure the following compounds can be prepared:
(2-formylaminoethyl)-2,3-dihydroxybenzene;
  NMR δ: 2.81 (t, 2H), 3.45 (t, 2H), 6.5-6.9 (m, 3H) 8.15 (S, 1H),
(2-formylaminoethyl)-2-hydrobenzene;
(2-formylaminoethyl)-3-hydroxybenzene;
(2-formylaminoethyl)-4-hydroxybenzene;
(2-formylaminoethyl)-2,4-dihydrobenzene;
(2-formylaminoethyl)-2,6-dihydroxybenzene;
(2-formylaminoethyl)-3,4-dihydroxybenzene;
(2-formylaminoethyl)-3,5-dihydroxybenzene, and
(2-formylaminoethyl)-2-hydroxy-5-bromobenzene.

EXAMPLE 7

(E)-N-[2-(2,5-diacetoxyphenyl)ethenyl]formamide (I, R=Ac, R$_1$=R$_2$=H, A=—CH=CH—, n=2)

To a cooled solution of erbstatin (1.792 g, 10 mmol) in dry pyridine (5 ml) is added acetic anhydride (4.084 g, 40 mmol) and the mixture maintained at 0°-5° C. overnight. The solvent is removed in vacuum, the residue dissolved in dichloromethane, the organic layer washed with water and then evaporated under reduced pressure. The crude product is crystallized from chloroform/methanol to yield pure title compound in 90% yield (2.37 g) with m.p. 146°-8° C.

C$_{13}$H$_{13}$NO$_5$ requires: C; 59.31, H; 4.98, N; 5.32. Found: C; 59.25, H; 4.95, N; 5.26.

According to the above described procedure the following compounds can be prepared:
(E)-N-[2-(2-acetoxyphenyl)ethenyl]formamide;
(E)-N-[2-(2,3-diacetoxyphenyl)ethenyl]formamide;
(E)-N-[2-(3,4-diacetoxyphenyl)ethenyl]formamide;
(E)-N-[2-(2-acetoxy-5-bromophenyl)ethenyl]formamide;
(E)-N-[2-(3-acetoxyphenyl)ethenyl]formamide;
(E)-N-[2-(4-acetoxyphenyl)ethenyl]formamide;
(E)-N-[2-(2,4-diacetoxyphenyl)ethenyl]formamide;
(E)-N-[2-(2,6-diacetoxyphenyl)ethenyl]formamide, and
(E)-N-[2-(3,5-diacetoxyphenyl)ethenyl]formamide.

We claim:

1. A process for the preparation of Erbstatin analogs and derivatives thereof, comprising the steps of:
   providing a compound of formula (II):

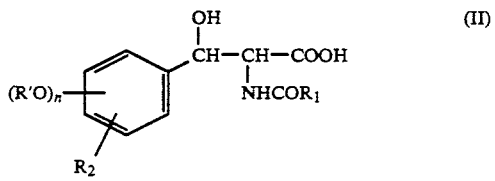

R' is lower alkyl
n is an integer of 1 to 3;
$R_1$ is hydrogen or a lower alkyl group, and
$R_2$ is a hydrogen or halogen atom,
dehydrative-decarboxylating the compound of formula (II); and
recovering a compound of formula (I)

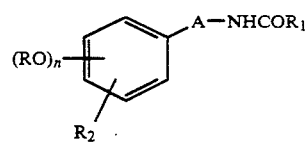

wherein
R is a lower alkyl
$R_1$, $R_2$ and n are as defined above, and
A is —CH=CH—.

2. A process as defined in claim 1, wherein the step of dehydrative-decarboxylating comprises the steps of
   providing the compound of formula (II) in an inert solvent;
   reacting the compound of formula (II) and N,N-dimethylformamide dimethylacetal at a temperature of about 0° to 100° C.

3. A process as defined in claim 1, wherein the step of dehydrative-decarboxylating comprises the steps of
   providing the compound of formula (II) in an inert solvent; and
   redox-condensing the compound of formula (II) with triphenylphosphine and diethyl azodicarboxylate.

4. A process as defined in claim 1, including the further step of hydrolyzing RO to produce a compound of formula (I) wherein R is hydrogen.

5. A process as defined in claim 1, wherein RO in formula (I) is initially lower alkoxy, further comprising the steps of:
   chilling a solution of the initial compound of formula (I) and an inert solvent to a temperature in the range of about −78° C. to about room temperature; and
   adding $BBr_3$ to the solution under an inert atmosphere, thereby hydrolyzing RO.

6. Process as defined in claim 1, including the further step of saturating the —CH=CH— group to form a compound of formula (I) wherein A is —$CH_2$—$CH_2$—.

7. Process as defined in claim 1, further comprising the steps of:
   placing a solution of a solvent selected from the group consisting of lower alkanol and water and the initial compound of formula (I) under a hydrogen atmosphere;
   adding a hydrogenation catalyst to the solution; and
   recovering a compound of formula (I) wherein A is —$CH_2$—$CH_2$—.

8. A process according to claim 4, wherein R in formula (I) is hydrogen, further comprising the step of converting R to a lower alkanoyl group.

9. A process according to claim 4, wherein R in formula (I) is hydrogen, further comprising the steps of:
   dissolving said compound of formula (I) in an organic base;
   adjusting the temperature of said solution to a range of about 0° to 50° C.;
   adding a member of the group consisting of a lower aliphatic carboxylic acid anhydride and a lower aliphatic carboxylic acid halide to the solution; and
   recovering a compound of formula (I) wherein R is a lower alkanoyl group.

* * * * *